US012728149B2

(12) United States Patent
Park et al.

(10) Patent No.: US 12,728,149 B2
(45) Date of Patent: Sep. 8, 2026

(54) PHARMACEUTICAL COMPOSITION FOR PREVENTING AND TREATING DEPRESSION, COMPRISING HERBAL MEDICINE COMPLEX EXTRACTS OF ZIZYPHI SPINOSI SEMEN, JUJUBAE FRUCTUS, HORDEI FRUCTUS GERMINATUS, GLYCYRRHIZAE RADIX ET RHIZOMA, ANGELICAE GIGANTIS RADIX, AND BETA VULGARIS AS ACTIVE INGREDIENTS

(71) Applicant: INDUSTRY-ACADEMIC COORPERATION FOUNDATION DAEGU HAANY UNIVERSITY, Gyeongsan-si (KR)

(72) Inventors: Jin Han Park, Daegu (KR); Ki Han Kwon, Gyeongsan-si (KR)

(73) Assignee: INDUSTRY-ACADEMIC COORPERATION FOUNDATION DAEGU HAANY UNIVERSITY, Gyeongsan-si (KR)

( * ) Notice: Subject to any disclaimer, the term of this patent is extended or adjusted under 35 U.S.C. 154(b) by 292 days.

(21) Appl. No.: 18/398,843

(22) Filed: Dec. 28, 2023

(65) Prior Publication Data

US 2024/0285720 A1 Aug. 29, 2024

(30) Foreign Application Priority Data

Feb. 28, 2023 (KR) ........................ 10-2023-0026580

(51) Int. Cl.

*A61K 36/21* (2006.01)
*A61K 36/232* (2006.01)
*A61K 36/484* (2006.01)
*A61K 36/725* (2006.01)
*A61K 36/8998* (2006.01)
*A61P 25/24* (2006.01)

(52) U.S. Cl.

CPC .......... *A61K 36/8998* (2013.01); *A61K 36/21* (2013.01); *A61K 36/232* (2013.01); *A61K 36/484* (2013.01); *A61K 36/725* (2013.01); *A61P 25/24* (2018.01); *A61K 2236/331* (2013.01)

(58) Field of Classification Search

CPC .. A61K 36/8998; A61K 36/21; A61K 36/232; A61K 36/484; A61K 36/725; A61K 2236/331; A61K 36/185; A61K 2236/37; A61K 36/899; A61K 2300/00; A61P 25/24; A23V 2200/322; A23V 2250/21; A23V 2300/14; A23V 2002/00; A23L 33/105

See application file for complete search history.

(56) References Cited

U.S. PATENT DOCUMENTS

2021/0052684 A1* 2/2021 Meyer .................. A61K 31/352

FOREIGN PATENT DOCUMENTS

WO WO-2017094916 A1 * 6/2017 .............. A61P 31/04

OTHER PUBLICATIONS

Wang JQ, Mao L. The ERK Pathway: Molecular Mechanisms and Treatment of Depression. Mol Neurobiol. Sep. 2019; vol. 56, pp. 6197-6205. doi: 10.1007/s12035-019-1524-3 (Year: 2019).*

Payne ME, Steck SE, George RR, Steffens DC. Fruit, vegetable, and antioxidant intakes are lower in older adults with depression. J Acad Nutr Diet. Dec. 2012; vol. 112, issue. 12, pp. 2022-2027. doi: 10.1016/j.jand.2012.08.026. (Year: 2012).*

Abubakar AR, Haque M. Preparation of Medicinal Plants: Basic Extraction and Fractionation Procedures for Experimental Purposes. J Pharm Bioallied Sci. Jan.-Mar. 2020; vol. 12, issue. 1, pp. 1-10. doi: 10.4103/jpbs.JPBS_175_19. (Year: 2020).*

Zhang, Zuoguang. "A Pharmaceutical Composition for Treating Depression and Method for Preparation Thereof". WO 2006099783 A1, filed Oct. 31, 2005, and published Sep. 28, 2006—English translation (Year: 2006) (Year: 2006).*

Yang, Chae Ha et al. "Composition Comprising Mixed Herbal Extract for Preventing and Treating Depression". KR 100881368 B1, filed Oct. 26, 2007 and published Feb. 2, 2009—English translation (Year: 2009).*

Wang, Yi-Fei et al. "Medicine Composition Containing Folium Artemisiae Argyifor Preventing And Treating Depression And Climacteric Syndrome". CN 105748666 A, filed Apr. 1, 2016 and published Jul. 13, 2016—English translation (Year: 2016).*

Gao, Song et al. "A New Use Traditional Chinese Medicine Composition In Preparation Of Antidepressant Medicine". CN 109550035 A, filed Dec. 30, 2018 and published Apr. 2, 2019—English translation (Year: 2019).*

* cited by examiner

*Primary Examiner* — Susan Hoffman
*Assistant Examiner* — Nashara L Moreau
(74) *Attorney, Agent, or Firm* — Sughrue Mion, PLLC

(57) ABSTRACT

Provided is composition for preventing and treating depression, including complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients. The complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* have an antidepressant effect and an effect on the expression of proteins related to antidepressant action. The complex extracts of the present disclosure may be effectively used as a composition for preventing and treating depression.

3 Claims, 3 Drawing Sheets

【Fig. 1】
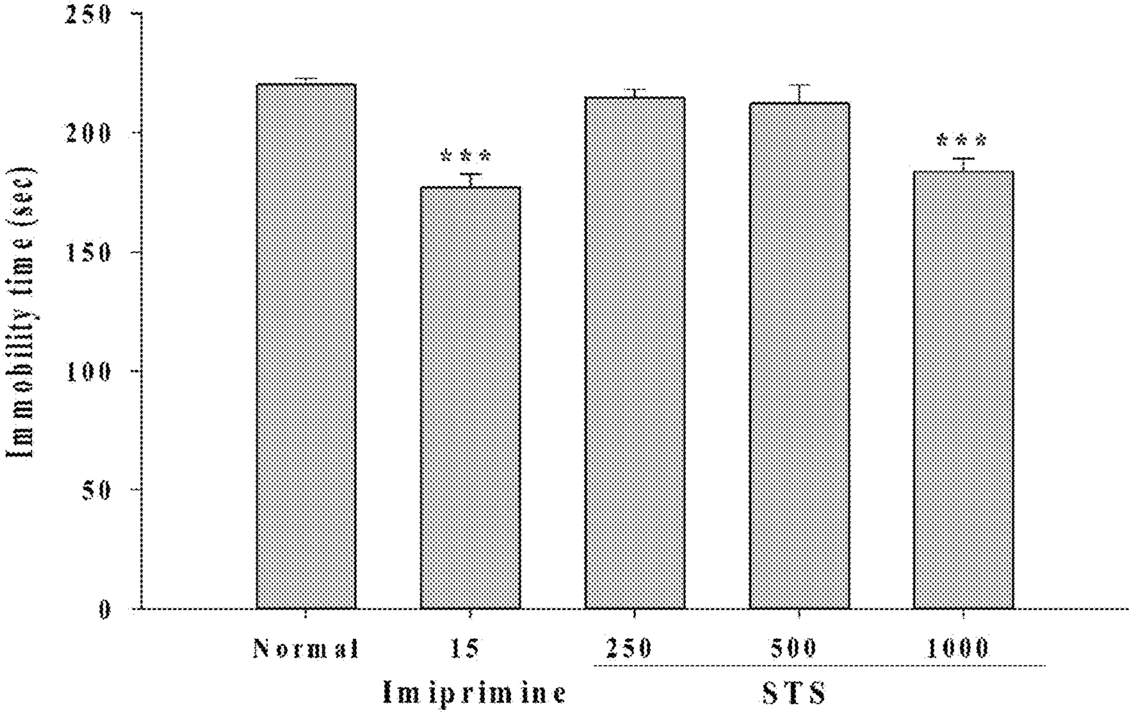
【Fig. 2】
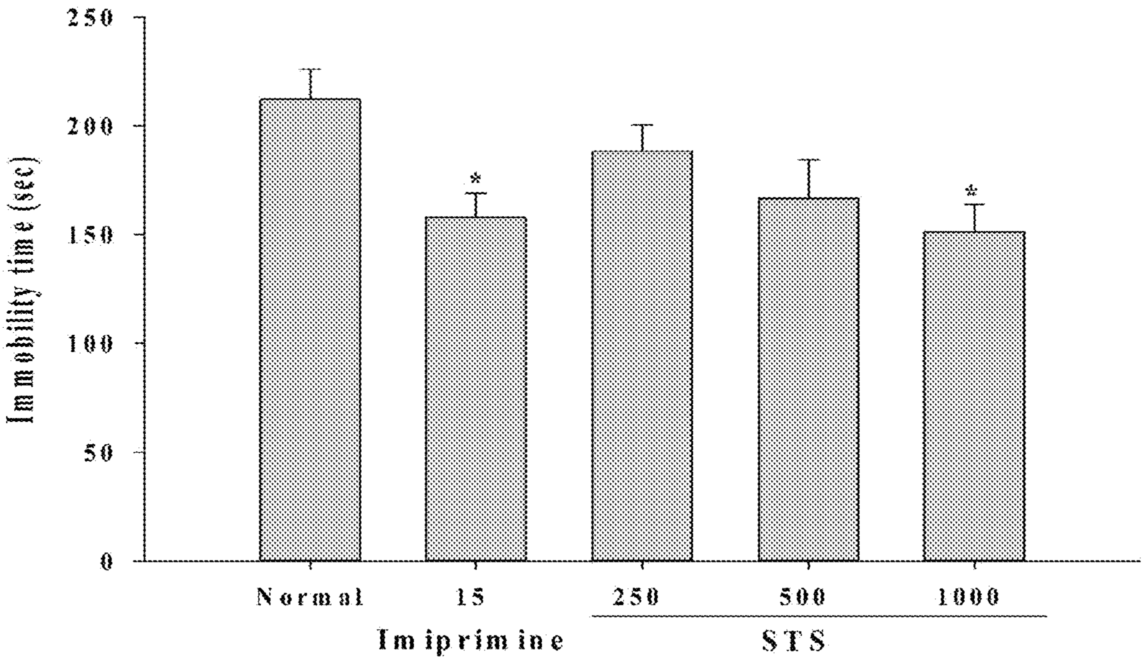

【Fig. 3】
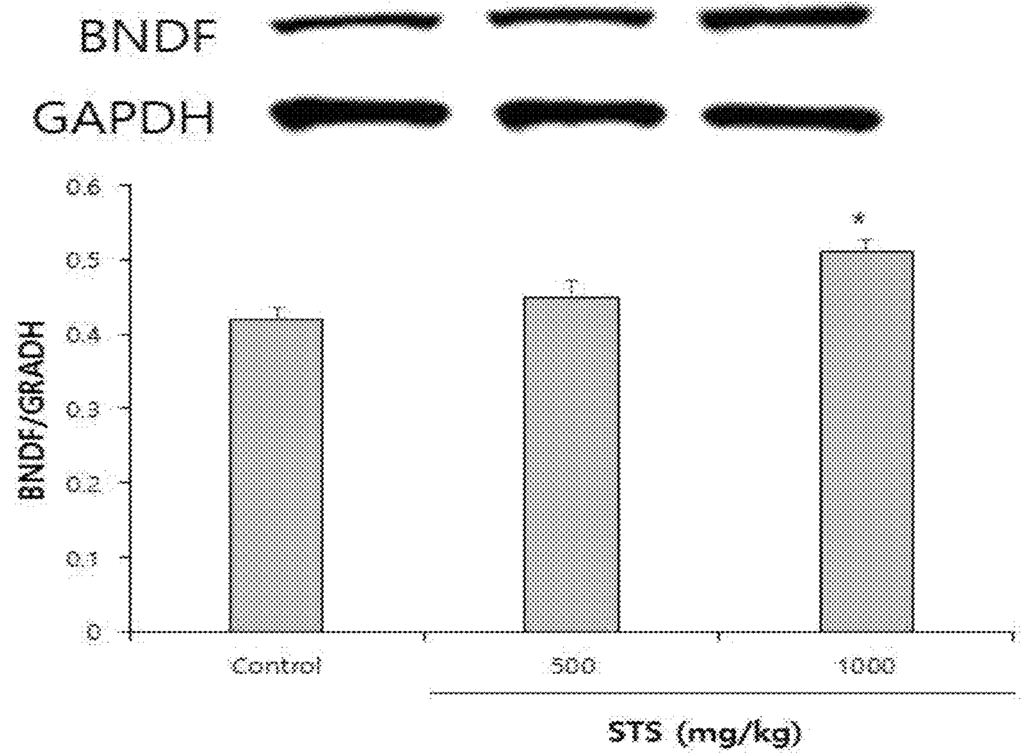
【Fig. 4】
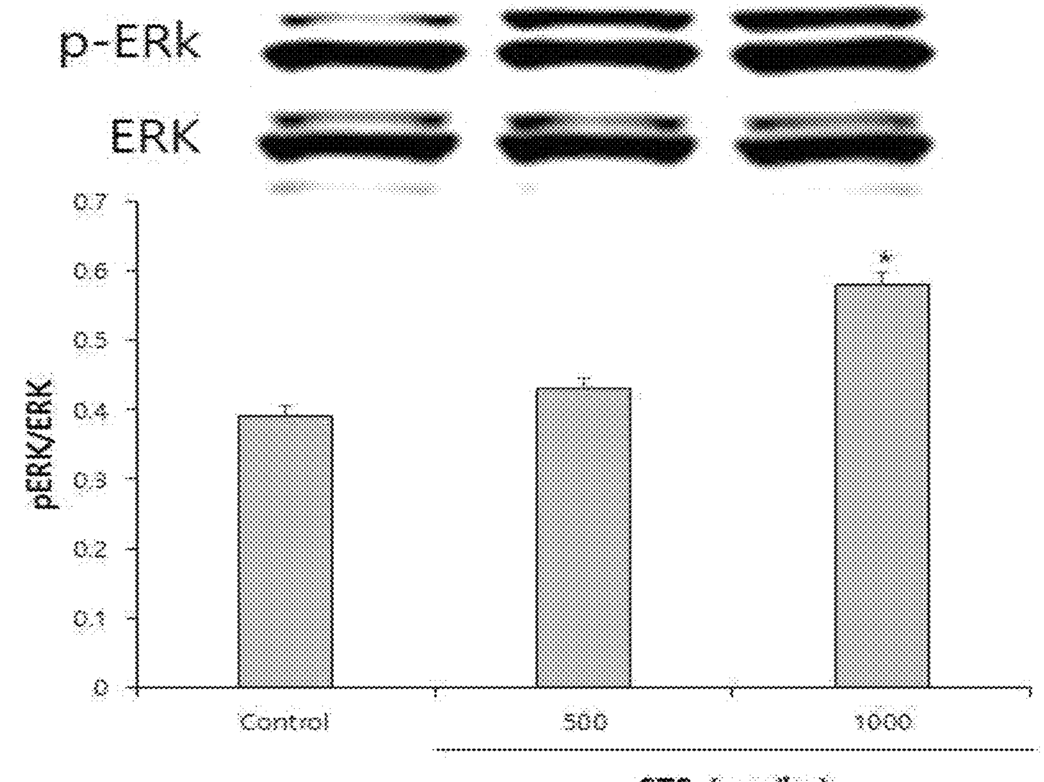

【Fig. 5】
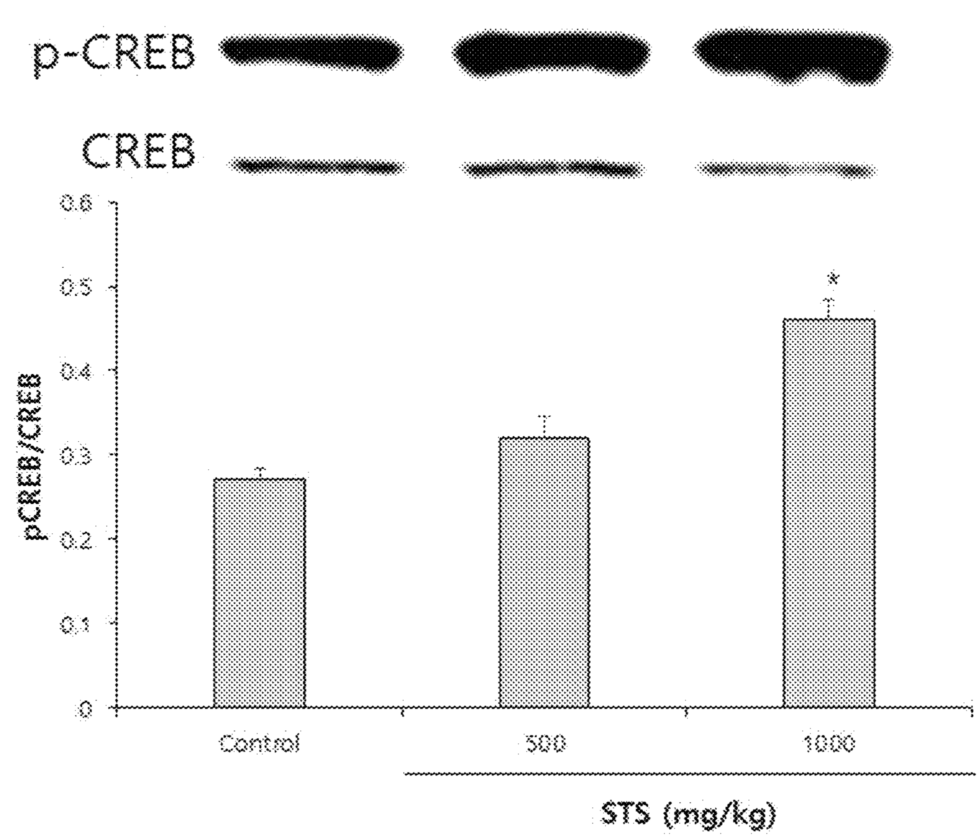

PHARMACEUTICAL COMPOSITION FOR PREVENTING AND TREATING DEPRESSION, COMPRISING HERBAL MEDICINE COMPLEX EXTRACTS OF ZIZYPHI SPINOSI SEMEN, JUJUBAE FRUCTUS, HORDEI FRUCTUS GERMINATUS, GLYCYRRHIZAE RADIX ET RHIZOMA, ANGELICAE GIGANTIS RADIX, AND BETA VULGARIS AS ACTIVE INGREDIENTS

CROSS-REFERENCE TO RELATED APPLICATIONS

This application is based on and claims priority from Korean Patent Application No. 10-2023-0026580, filed on Feb. 28, 2023 with the Korean Intellectual Property Office, the disclosure of which is incorporated herein in its entirety by reference.

TECHNICAL FIELD

The present disclosure relates to a pharmaceutical composition for preventing and treating depression, including herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

BACKGROUND

Depression is a serious disease that causes a variety of cognitive and psychosomatic symptoms with low motivation and depression as main symptoms, leading to a decline in daily functions and changes in emotions, thoughts, physical conditions, and behavior. The depression is different from temporary depression and is not an expression of personal weakness or not eliminated by will. That is, the depression is a brain nervous system disease caused by an imbalance of neurotransmitters, etc., and is considered as not a simple psychological symptom but a disease that is able to be treated only by taking drugs.

The cause of depression is not yet clear, and it is known that the depression is caused by a chemical imbalance in monoamine-based neurotransmitters, such as dopamine, serotonin, and norepinephrine. Based on research into these disease causes, a selective serotonin reuptake inhibitor (SSRI), a serotonin and noradrenaline reuptake inhibitor (SNRI), a monoamine oxidase inhibitor (MAOi), etc. capable of restoring the balance of monoamine neurotransmitters were developed, and account for most of the today's depression therapy market.

Antidepressants currently used have limitations such as a delay in the onset of drug efficacy, low patient's response rate to drugs, etc., and thus, research is needed to develop antidepressants with a rapid onset time of drug efficacy and a wide range of mechanisms.

In oriental medicine, mental disorders such as depression and anxiety are recognized as being caused by blood deficiency and qi deficiency or heat in the liver, heart, and spleen, and depression, anxiety, insomnia, multiple dreams, fear, convulsions, frenzy, and mental or emotional disorder occur due to these causes. In the oriental medicine, these mental and nervous disorders are mainly treated with a group of drugs called tranquilizers, which reduce anxiety and have a sedative and hypnotic effect.

Meanwhile, there has not been disclosed an antidepressant effect of herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris*.

*Zizyphi spinosi Semen* is a medicinal herb made from the seeds of jujube of Rhamnaceae, and it is known that ingredients thereof contain verulin, verulic acid, jujubosides A and B, sitosterol, ebelinlactone, oleic acid, linoleic acid, palmitic acid, etc. It is known that its pharmacological effects include sedation, hypnosis, blood pressure drop, analgesic, body temperature drop action, antioxidant action, immune boosting action, uterine stimulating action, swelling suppressing action in burn affected areas, etc.

*Jujubae Fructus* is the fruit of *Zizyphus jujuba* MILL. var. inermis REHD. of Rhamnaceae, and it is known that ingredients thereof contain proteins, sugars, organic acids, vitamin A, vitamin B2, vitamin C, and trace amounts of calcium, phosphorus, and iron, and it is known that its pharmacological effects include tonic, energetic, diuretic, muscle-strengthening, liver-protecting, immune-boosting, and tension-relieving effects.

*Hordei Fructus Germinatus* is derived from sprouted ripe fruits of barley *Hordeum vulgare* Linne var. *hexastichon* Aschers (Gramineae) and is effective in digestive disorders and lack of milk secretion. Its pharmacological effects are known to promote digestion and lower blood sugar levels.

*Glycyrrhizae Radix* et Rhizoma is a generally safe herbal medicine frequently applied in many complex prescriptions in oriental pharmacology. *Glycyrrhizae Radix* et Rhizoma is mixed into other prescriptions for the purpose of not only detoxifying drugs, relieving the strong properties of herbal medicines, and helping other drugs harmonize well with each other within the prescription, but also relieving various types of pain, and is used to lubricate the lungs, have an antipyretic effect, treat sore throats, help with weakness of the nasogastric function, and stabilize the mind to have the effect of detoxifying toxic substances.

*Angelicae Gigantis Radix* is a representative medicinal plant frequently used among herbal medicines, and is known to have outstanding efficacy in replenishing energy and treating gynecological diseases, help improve blood circulation and bowel movement, and be effective in improving constipation and indigestion.

*Beta vulgaris* is known to have anticancer effects, and it is known that an ingredient, betalain contained in *Beta vulgaris* roots has an anti-cancer effect to prevent breast cancer and prostate cancer.

SUMMARY

The present disclosure has been made in an effort to provide a pharmaceutical composition for preventing and treating depression, including herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

The present disclosure has also been made in an effort to provide a health functional food composition for preventing or alleviating depression, including herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

An exemplary embodiment of the present disclosure provides a pharmaceutical composition for preventing and treating depression, including complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

In an exemplary embodiment of the present disclosure, the complex extracts may be extracted for 1 to 3 hours at 70 to 110° C. by adding 3 to 7-fold distilled water to each herbal medicine and mixed, but are not limited thereto.

In an exemplary embodiment of the present disclosure, the complex extracts may be prepared by extracting a mixture including *Zizyphi spinosi Semen* of 2 to 4 parts by weight, *Jujubae Fructus* of 1 to 3 parts by weight, *Hordei Fructus Germinatus* of 1 to 3 parts by weight, *Glycyrrhizae Radix* et Rhizoma of 0.5 to 1.5 parts by weight, *Angelicae Gigantis Radix* of 0.5 to 1.5 parts by weight and *Beta vulgaris* of 0.5 to 1.5 parts by weight, but are not limited thereto.

In an exemplary embodiment of the present disclosure, the complex extracts may increase the protein expression of Brain-Derived Neurotrophic Factor, Extracellular Signal-Regulated Kinase and cAMP Response Element-Binding Protein, but are not limited thereto.

In addition, another exemplary embodiment of the present disclosure provides a health functional food composition for preventing or alleviating depression, including complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

According to the exemplary embodiments of the present disclosure, it is confirmed that the herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* have an antidepressant effect and an effect on the expression of proteins related to antidepressant action. Since the herbal medicine complex extracts of the present disclosure have an effect of preventing and treating depression, the herbal medicine complex extracts may be effectively used as a pharmaceutical composition for preventing and treating depression and a health functional food composition for preventing or alleviating depression.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a diagram illustrating a forced swimming test result of mice according to treatment with herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* in an exemplary embodiment of the present disclosure.

FIG. 2 is a diagram illustrating a tail suspension test result of mice according to treatment with herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* in an exemplary embodiment of the present disclosure.

FIG. 3 is a diagram illustrating a BDNF protein detection result according to treatment with herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* in an exemplary embodiment of the present disclosure.

FIG. 4 is a diagram illustrating an ERK protein detection result according to treatment with herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* in an exemplary embodiment of the present disclosure.

FIG. 5 is a diagram illustrating a CREB protein detection result according to treatment with herbal medicine complex extracts including *Zizyphi spinosi Semen, Jujubae Fructus, Hordei Fructus Germinatus, Glycyrrhizae Radix* et Rhizoma, *Angelicae Gigantis Radix*, and *Beta vulgaris* in an exemplary embodiment of the present disclosure.

DETAILED DESCRIPTION

Hereinafter, an exemplary embodiment of the present disclosure will be described in detail with reference to the accompanying drawings. However, the following exemplary embodiments are presented as examples for the present disclosure, and when it is determined that a detailed description of well-known technologies or configurations known to those skilled in the art may unnecessarily obscure the gist of the present disclosure, the detailed description thereof may be omitted, and the present disclosure is not limited thereto. Various modifications and applications of the present disclosure are possible within the description of claims to be described below and the equivalent scope interpreted therefrom.

In addition, terminologies used in the present disclosure are a terminologies used to properly express preferred embodiments of the present disclosure, which may vary according to a user, an operator's intention, or customs in the art to which the present disclosure pertains. Accordingly, definitions of the terminologies need to be described based on contents throughout this specification. Throughout the specification, when a part "comprises" a certain component, it is meant that the part may further include other components, not excluding other components, unless explicitly described to the contrary.

Throughout this specification, '%' used to indicate the concentration of a specific material is solid/solid (w/w) %, solid/liquid (w/v) %, and liquid/liquid (v/v) %, unless otherwise stated.

In an aspect, the present disclosure provides a pharmaceutical composition for preventing and treating depression, including herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

The extract according to the present disclosure may be obtained and used by extraction and separation from the nature using extraction and separation methods known in the art. The "extract" as defined in the present disclosure is extracted from *Zizyphi spinosi Semen, Jujubae Fructus, Hordei Fructus Germinatus, Glycyrrhizae Radix* et Rhizoma, *Angelicae Gigantis Radix*, and *Beta vulgaris* using a suitable solvent, and includes all extracts, for example, a crude extract, a polar solvent-soluble extract, and a non-polar solvent-soluble extract. The suitable solvent for extracting the extracts from *Zizyphi spinosi Semen, Jujubae Fructus, Hordei Fructus Germinatus, Glycyrrhizae Radix* et Rhizoma, *Angelicae Gigantis Radix*, and *Beta vulgaris* may use any pharmaceutically acceptable organic solvent, and may use water or an organic solvent, but is not limited thereto. For example, various solvents such as purified water, alcohols having carbon atoms 1 to 4 including methanol, ethanol, propanol, isopropanol, butanol, etc., acetone, ether, benzene, chloroform, ethyl acetate, methylene chloride, hexane, cyclohexane, etc. may be used alone or in combination. As an extraction method, any one of methods such as hot water extraction, chilling extraction, reflux cooling extraction, solvent extraction, steam distillation, ultrasonic extraction, elution, and compression may be selected and used. In addition, a desired extract may also be additionally subjected to a conventional fractionation process or purified using a conventional purification method.

There is no limitation to a preparation method of the extracts of the present disclosure, and any known preparation method may be used. For example, the extracts included in the composition of the present disclosure may be prepared with primary extracts extracted by the hot water extraction or solvent extraction method in a powder state by additional processes such as distilling under reduced pressure and freeze-drying or spray-drying. In addition, fractions may also be obtained by further purifying the primary extracts using various chromatography, such as silica gel column chromatography, thin layer chromatography, and high performance liquid chromatography. Accordingly, in the present disclosure, the extract is a concept that includes all extracts, and fractioned and purified products that are obtained in each step of extraction, fractionation, or purification, and dilutions, concentrates, or dried products thereof.

In the present disclosure, the herbal medicine complex extracts may be prepared by adding distilled water 3 to 7 times, preferably 4 to 6 times, more preferably 5 times as much as each herbal medicine and then extracting and mixing the herbal medicines at 70 to 110° C., preferably 80 to 100° C. for 1 to 3 hours, preferably 1.5 to 2.5 hours, more preferably 2 hours, but are not limited thereto.

In the present disclosure, the herbal medicine complex extracts may be prepared by extracting a mixture including *Zizyphi spinosi Semen* of 2 to 4 parts by weight, *Jujubae Fructus* of 1 to 3 parts by weight, *Hordei Fructus Germinatus* of 1 to 3 parts by weight, *Glycyrrhizae Radix* et Rhizoma of 0.5 to 1.5 parts by weight, *Angelicae Gigantis Radix* of 0.5 to 1.5 parts by weight and *Beta vulgaris* of 0.5 to 1.5 parts by weight, but are not limited thereto.

In the present disclosure, the herbal medicine complex extracts may increase protein expression of Brain-Derived Neurotrophic Factor, Extracellular Signal-Regulated Kinase, and cAMP Response Element-Binding Protein, but are not limited thereto.

As used in the present disclosure, the term "Brain-Derived Neurotrophic Factor (BDNF)" is a protein in the brain and is one of a group of neurotrophic factors that are part of growth factors. When the BDNF in the hippocampus acts, emotion, memory, and cognitive functions are increased, and this protein has been studied in depression and dementia research, etc.

As used in the present disclosure, the term "hippocampus" is located inside the temporal lobe and exists beneath the cerebral cortex. The hippocampus plays a role in learning, memory, and recognition of new things.

As used in the present disclosure, the term "Extracellular Signal-Regulated Kinase (ERK)" is an enzyme that is activated by various stimuli, such as growth factors, cytokines, and viral infections.

As used in the present disclosure, the term "cAMP Response Element-Binding Protein (CREB)" plays an important role in causing the transcriptional activity of various transcriptional regulators.

In an aspect, the present disclosure provides a health functional food composition for preventing or alleviating depression, including herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

The food composition of the present disclosure may contain various flavoring agents, natural carbohydrates, or the like as additional ingredients, like conventional food compositions, in addition to the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients.

Examples of the above-described natural carbohydrates may include general sugars, such as monosaccharides, such as glucose, fructose, etc.; disaccharides, such as maltose, sucrose, etc.; and polysaccharides, such as dextrin, cyclodextrin, etc., and sugar alcohols such as xylitol, sorbitol, erythritol, etc. The above-described flavoring agents may be advantageously used with natural flavoring agents (tauumatin), stevia extracts (e.g., rebaudioside A, glycyrrhizin, etc.), and synthetic flavoring agents (saccharin, aspartame, etc.). The food composition of the present disclosure may be formulated in the same manner as the following pharmaceutical composition to be used as functional foods or added to various foods. The foods capable of adding the composition of the present disclosure may include, for example, beverages, meat, chocolate, foods, confectionery, pizza, ramen, other noodles, gums, candies, ice creams, alcohol beverages, vitamin complexes, health food supplements, etc.

In addition, the food composition may contain various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohols, a carbonic acid agent used in a carbonated drink, etc., in addition to the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* as active ingredients. In addition, the food composition of the present disclosure may contain pulp for preparing natural fruit juice, fruit juice beverages, and vegetable beverages.

The functional food composition of the present disclosure may be prepared and processed in the form of tablets, capsules, powders, granules, liquids, pills, etc. In the present disclosure, the 'health functional food composition' refers to foods prepared and processed by using raw materials or ingredients with functionality, which are useful for the human body according to the Art on Health Functional Foods No. 6727, and means foods taken for adjusting nutrients for the structures and functions of the human body or obtaining a useful effect on health applications such as physiological actions. The health functional food of the present disclosure may include conventional food additives, and the suitability as the food additives is determined by the specifications and standards for the corresponding item in accordance with the general rules of the Food Additive Codex, general test methods, etc., that are approved by the Food and Drug Administration, unless otherwise specified. The items disclosed in the "Food Additives Codex" may include, for example, chemical composites such as ketones, glycine, calcium citrate, nicotinic acid, cinnamic acid, etc.; natural additives such as persimmon color, licorice extract, crystal cellulose, Kaoliang color, guar gum, etc.; mixed formulations such as sodium L-glutamic acid formulations, noodle additive alkali agents, preservative formulations, tar color formulations, etc. For example, the health functional food in the form of tablets may formed by granulating a mixture obtained by mixing the active ingredients of the present disclosure with an excipient, a binder, a disintegrant, and other additives in a conventional manner, and then compression-molding the mixture by adding a slip modifier and the like, or directly compressing the mixture. In addition, the health functional food in the form of tablets may also contain a flavors enhancer or the like as needed. In the health functional food in the form of capsules, hard capsules may be prepared by filling a mixture mixed with the active ingredient of the present disclosure and additives such as excipients into conventional hard capsules, and soft capsules may be prepared by filling a mixture mixed with the active ingredient of the present disclosure and additives such as excipients into capsule bases such as gelatin. The soft capsules may contain a plasticizer such as glycerin or sorbitol, a colorant, a preservative, and the like, if necessary. The health functional food in the form of pills may be prepared by molding a mixture mixed with the active ingredients of the present disclosure with an excipient, a binder, a disintegrant, etc. by existing known methods, and may also be coated with white sugar or other coating agents or surface-coated with materials such as starch and talc, if necessary. The health functional food in the form of granules may be prepared by granulating a mixture mixed with the active ingredients of the present disclosure with an excipient, a binder, a disintegrant, etc. by existing known methods and may contain a flavoring agent, a flavors enhancer, etc., if necessary.

As described above, the specific examples of the present disclosure have been described, but those skilled in the art understanding the spirit of the present disclosure will be able to easily propose other degenerate inventions or other examples included in the scope of the present disclosure by adding, changing, and deleting other elements within the same technical scope. Therefore, it should be appreciated that the examples described above are illustrative in all aspects and are not restricted. The scope of the present disclosure is represented by claims to be described below rather than the detailed description, and it is to be interpreted that the meaning and scope of the claims and all the changes or modified forms derived from the equivalents thereof come within the scope of the present disclosure.

<Preparation Example 1> Preparation for Animal Experiment

All animal experiment procedures of the present disclosure were conducted in compliance with the preliminary review and ethics regulations of the Animal Experiment Ethics Committee of Daegu Haany University. 4-week-old male ICR mice (SPF/VAF CrljBgi:CD-1) were supplied from the Daehan Biolink (Chungcheongbuk-do, Korea), and adapted and used for 7 days in the pharmacology animal laboratory of Daegu Haany University. Each group consisted of 8 mice, and 5 mice were housed in polycarbonate mice cages and bred in a breeding room where a temperature of 23±1° C., humidity of 50±5%, and lighting time of 07:00 to 19:00 (12-hour cycle) were kept constant. During the adaptation period, feed and water were supplied without restrictions.

<Example 1> Preparation of Herbal Medicine Complex Extracts

An herbal medicine complex extract sample including *Zizyphi spinosi Semen, Jujubae Fructus, Hordei Fructus Germinatus, Glycyrrhizae Radix* et Rhizoma, *Angelicae Gigantis Radix*, and *Beta vulgaris* was purchased and used from Siwoo Co., Ltd. (Gyeongsan, Gyeongsangbuk-do, Korea). The prescription was configured as shown in Table 1 below, and herbal medicine complex extracts were prepared by adding 5-fold distilled water to the mixed herbal medicine and extracting the mixture at 80 to 100° C. for 2 hours.

TABLE 1

| Herbs | Pharmacognosy name | Dose (g) |
|---|---|---|
| Zizyphus spinosi | *Zizyphi spinosi Semen* | 1,500 |
| Jujuba | *Jujubae Fructus* | 1,000 |
| Malt | *Hordei Fructus Germinatus* | 1,000 |
| Licorice | *Glycyrrhizae Radix* et Rhizoma | 500 |
| Angelica | *Angelicae Gigantis Radix* | 500 |
| Beet | *Beta vulgaris* | 500 |
| Total | | 5,000 |

<Experimental Example 1> Administration of Herbal Medicine Complex Extract Sample In an experimental group, the herbal medicine complex extract sample of *Zizyphi spinosi Semen, Jujubae Fructus, Hordei Fructus Germinatus, Glycyrrhizae Radix* et Rhizoma, *Angelicae Gigantis Radix*, and *Beta vulgaris* prepared Example 1 was orally administered to 8 experimental animals for each group prepared in Preparation Example 1 at 250, 500, and 1000 mg/kg for 1 week, and on day 7 of administration, the animal experiment was conducted 60 minutes after administration of the herbal medicine complex extract sample.

A positive control group consisted of mice administered intraperitoneally with 15 mg/kg of imipramine for 1 week, and the animal experiment was conducted 30 minutes after intraperitoneal administration of imipramine on day 7 of administration.

A control group consisted of mice orally administered with a saline solution for 1 week, and each group consisted of 8 mice.

<Experimental Example 2> Confirmation of Antidepressant Effect

2-1. Forced Swimming Test (FST)

In order to verify whether there was an antidepressant effect of the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* of the present disclosure, a forced swimming test (FST) was performed using experimental animals. The antidepressant effect was determined by measuring the immobility time during the forced swimming test, and it was meant that shorter the immobility time, the greater the antidepressant effect.

A transparent acrylic cylindrical water tank with a height of 25 cm and a diameter of 11 cm was manufactured, and added with water at 25±1° C. The mouse was forced into the water at a level where its tail did not touch the bottom of the water tank and adapted for 2 minutes. After adaptation, the immobility time was measured using the EthoVision program (Noldus Information Technology, Wageningen, Netherlands) for 4 minutes to measure the antidepressant effect, and shown in Table 2 and FIG. 1 below.

TABLE 2

| Group | Dose (mg/kg) | Immobility time (sec) |
|---|---|---|
| Normal (Control group) | 0 | 220.20 ± 2.60 |
| Imipramine (Positive control group) | 15 | 177.01 ± 5.67 |
| Herbal medicine complex extracts | 250 | 214.76 ± 3.37 |
| (Experimental group) | 500 | 212.26 ± 7.71 |
| | 1,000 | 177.01 ± 5.67 |

As shown in Table 2 and FIG. 1, the immobility time of the control group was the longest, and the immobility time of the positive control group administered with imipramine was reduced compared to the control group. In addition, the immobility time of the experimental group was reduced compared to the control group, and the immobility time was the shortest in the experimental group administered with 1000 mg/kg of the herbal medicine complex extract sample.

As a result, it was confirmed that the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* had the activity capable of preventing, alleviating, and treating depression and may be used as antidepressants.

2-2. Tail Suspension Test (TST)

In order to verify whether there was an antidepressant effect of the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* of the present disclosure, a tail suspension test (TST) was performed using experimental animals. The antidepressant effect was determined by measuring the immobility time during the tail suspension test, and experimental animals with tails alternated mobility and immobility, and the shorter the immobility time, there was the antidepressant effect.

After drug administration was completed, a tape was attached to 1 cm from the tip of the mouse's tail at the edge of a 50 cm-high table, and the immobility time was measured for 10 minutes, as shown in Table 3 and FIG. 2.

TABLE 3

| Group | Dose (mg/kg) | Immobility time (sec) |
|---|---|---|
| Normal (Control group) | | 212.21 ± 13.76 |
| Imipramine (Positive control group) | 15 | 157.82 ± 11.02 |
| Herbal medicine complex extracts | 250 | 188.40 ± 3.37 |
| Experimental group) | 500 | 166.57 ± 7.71 |
| | 1,000 | 151.03 ± 12.72 |

As shown in Table 3 and FIG. 2, the immobility time of the control group was the longest, and the immobility time of the positive control group administered with imipramine was decreased compared to the control group. In addition, the immobility time of the experimental group was decreased compared to the control group, and the immobility time of the experimental group administered with 1000 mg/kg of the herbal medicine complex extract sample was the shortest.

As a result, it was confirmed that the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* had the activity capable of preventing, alleviating, and treating depression and may be used as antidepressants.

2-3. Western Blot Test

In order to verify whether the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* affected the protein expression of Brain-Derived Neurotrophic Factor (BDNF), Extracellular Signal-Regulated Kinase (ERK), and cAMP Response Element-Binding Protein (CREB), which were representative signaling pathways related to antidepressant action, a Western blot test was performed to detect BDNF, ERK and CREB proteins.

One hour after administration of the herbal medicine complex extracts, all experimental animals were sacrificed, hippocampal tissues were extracted, and proteins were isolated. The isolated proteins were quantified and separated by electrophoresis on a 12% polyacrylamide gel. After separation, the proteins were moved using a polyvinylidene fluoride (PVDF) membrane. The membrane was blocked with 5% skim milk for 1 hour and reacted with primary antibodies BDNF, p-ERK, ERK, pCREB, CREB, and GAPDH at 4° C. for 24 hours. The membrane was washed three times using Tris-buffered saline with 0.1% tween 20 (TBST) and reacted with a secondary antibody for 1 hour at room temperature. Observation of the separated proteins was photographed using the LAS 4000 mini system (GE Healthcare™, VA, USA) and was shown in FIGS. 3 to 5.

As shown in FIGS. 3 to 5, it was confirmed that the expression of BDNF, pERK, and pCREB in hippocampal tissue was increased in the group administered with 1,000 mg/kg of the herbal medicine complex extracts compared to the control group.

As a result, it was confirmed that the herbal medicine complex extracts of *Zizyphi spinosi Semen, Jujubae Fructus, Hordei Fructus Germinatus, Glycyrrhizae Radix* et Rhizoma, *Angelicae Gigantis Radix*, and *Beta vulgaris* showed increased expression of BDNF, ERK, and CREB proteins, which were representative signaling pathways related to antidepressant action, and thus, the herbal medicine complex extracts had the activity capable of preventing, alleviating, and treating depression and may be used as antidepressants.

The present disclosure has been described above with reference to preferred Examples and Experimental Examples thereof. It will be understood to those skilled in the art that the present disclosure may be implemented as modified forms without departing from an essential characteristic of the present disclosure. Therefore, the disclosed exemplary embodiments should be considered in an illustrative viewpoint rather than a restrictive viewpoint. The scope of the present disclosure is illustrated by the appended claims rather than by the foregoing description, and all differences within the scope of equivalents thereof should be construed as being included in the present disclosure.

What is claimed is:

1. A method for treating depression, comprising administering to a subject in need thereof a composition comprising an active ingredient consisting of extracts of *Zizyphi spinosi Semen, Jujubae Fructus, Hordei Fructus Germinatus, Glycyrrhizae Radix et Rhizoma, Angelicae Gigantis Radix*, and *Beta vulgaris,* wherein the subject requires increasing a protein expression of Brain-Derived Neurotrophic Factor, Extracellular Signal-Regulated Kinase and cAMP Response Element-Binding Protein.

2. The method for treating depression of claim 1, wherein the extracts are extracted for 1 to 3 hours at 70 to 110° C. by adding 3 to 7-fold distilled water to each of the *Zizyphi spinosi Semen*, the *Jujubae Fructus*, the *Hordei Fructus Germinatus*, the *Glycyrrhizae Radix* et Rhizoma, the *Angelicae Gigantis Radix*, and the *Beta vulgaris*.

3. The method for treating depression of claim 1, wherein the extracts are prepared by extracting a mixture including the *Zizyphi spinosi Semen* in 2 to 4 parts by weight, the *Jujubae Fructus* in 1 to 3 parts by weight, the *Hordei Fructus Germinatus* in 1 to 3 parts by weight, the *Glycyrrhizae Radix* et Rhizoma in 0.5 to 1.5 parts by weight, the *Angelicae Gigantis Radix* in 0.5 to 1.5 parts by weight, and the *Beta vulgaris* in 0.5 to 1.5 parts by weight.

* * * * *